(12) United States Patent
Müller et al.

(10) Patent No.: US 6,767,333 B1
(45) Date of Patent: Jul. 27, 2004

(54) SAFETY DEVICE FOR A BLOOD TREATMENT MACHINE AND A METHOD OF INCREASING THE SAFETY OF A BLOOD TREATMENT MACHINE

(75) Inventors: Carsten Müller, Euerbach (DE); Christoph Bardorz, Rottendorf (DE)

(73) Assignee: Fresenius Medical Care Deutschland, Bad Homburg (DE)

( * ) Notice: Subject to any disclaimer, the term of this patent is extended or adjusted under 35 U.S.C. 154(b) by 147 days.

(21) Appl. No.: 09/649,213

(22) Filed: Aug. 28, 2000

(30) Foreign Application Priority Data

Aug. 27, 1999 (DE) ......................................... 199 40 624

(51) Int. Cl.⁷ ........................... A61M 37/00; C02F 1/44
(52) U.S. Cl. .................. 604/6.09; 604/4.01; 604/6.11; 210/646
(58) Field of Search ................................ 210/645–646, 210/321.65; 604/5.01, 4.01, 5.04, 6.11, 6.09

(56) References Cited

U.S. PATENT DOCUMENTS

| | | | |
|---|---|---|---|
| 4,202,764 A | * 5/1980 | Afflerbaugh et al. ... | 210/321.65 |
| 4,381,999 A | * 5/1983 | Boucher et al. ......... | 210/637 |
| 4,936,980 A | * 6/1990 | Harada et al. ........ | 210/321.65 |
| 5,431,811 A | * 7/1995 | Tusini et al. ............. | 210/117 |
| 5,589,077 A | * 12/1996 | Matsuda et al. .......... | 134/902 |
| 5,660,722 A | * 8/1997 | Nederlof ................. | 210/321.65 |

FOREIGN PATENT DOCUMENTS

| | | |
|---|---|---|
| DE | 34 16 057 | 10/1985 |
| DE | 42 39 937 | 6/1994 |

OTHER PUBLICATIONS

F. von der Haar et al., "Microprocessor–controlled, volumetric ultrafiltration with a hemodialysis unit," Biomed. Technik, 29 (1984), pp. 141–146.

* cited by examiner

Primary Examiner—Angela D. Sykes
Assistant Examiner—Leslie R Deak
(74) Attorney, Agent, or Firm—Kenyon & Kenyon

(57) ABSTRACT

A device and method for increasing the safety of an extracorporeal blood treatment machine are based on monitoring transmembrane pressure. The transmembrane pressure measured by a measuring device during the treatment is compared with an upper limit transmembrane pressure $L_1$ and a lower limit transmembrane pressure $L_2$ which define a monitoring window. If the transmembrane pressure is outside this monitoring window, an alarm is triggered by an alarm device. The monitoring window is shifted as a function of the ultrafiltration rate. To determine the window limits, the transmembrane pressure is established after a change in the ultrafiltration rate is calculated. Thereafter, the window limits are determined on the basis of the expected transmembrane pressure.

5 Claims, 1 Drawing Sheet

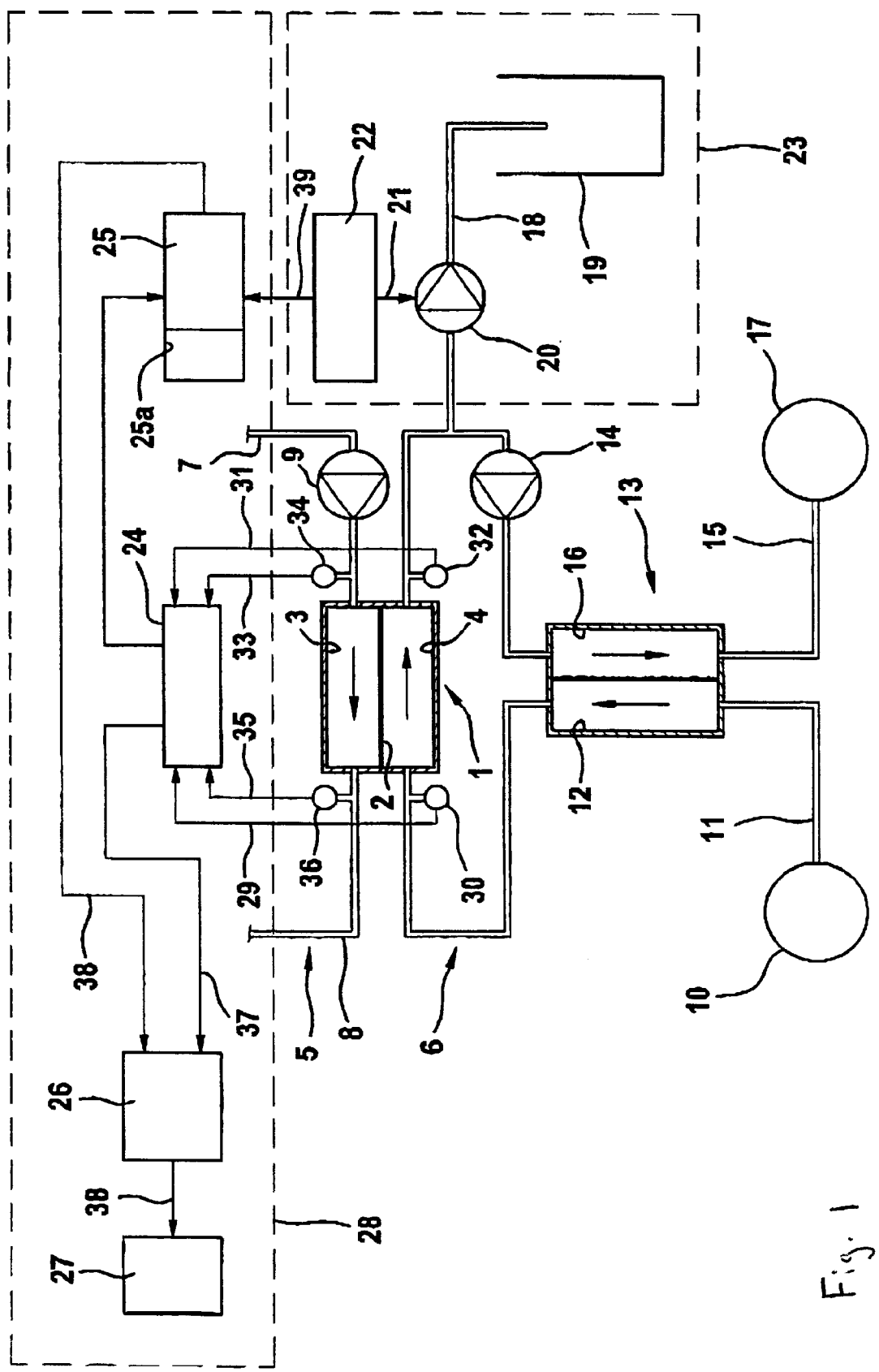

SAFETY DEVICE FOR A BLOOD TREATMENT MACHINE AND A METHOD OF INCREASING THE SAFETY OF A BLOOD TREATMENT MACHINE

FIELD OF THE INVENTION

The present invention relates to a safety device for an extracorporeal blood treatment machine and, more particularly, to such a device for monitoring the ultrafiltration rate for a hemodialysis, hemofiltration or hemodiafiltration machine. The invention also relates to a method of increasing the safety of an extracorporeal blood treatment machine.

BACKGROUND OF THE INVENTION

Various methods of surgical purification or treatment of blood are used on patients with chronic renal failure. Such methods are used to remove undesirable substances that typically pass through a healthy person's urine. The methods are also used to remove excess body fluid in the patients. Diffusive mass transport is the predominant mechanism in hemodialysis (HD), while convective mass transport through the membrane is involved in hemofiltration (HF). Hemodiafiltration (HDF) is a combination of both methods.

Removing excess body fluid by ultrafiltration is an essential component of dialysis therapy. With the standard form of therapy today, either a fixed ultrafiltration rate (UFR) or a fixed time characteristic of the ultrafiltration rate (UF profile) is selected. The ultrafiltration rate and the ultrafiltration volume during a treatment affect cardiovascular regulation and the fluid compartment of the patient's body. Therefore, ultrafiltration is critical for safety. With uncontrolled withdrawal of fluid at the rate of several liters/hour (L/h), a significant decrease in blood volume may be reached after a few minutes. Such a decrease may result in a severe drop in blood pressure necessitating intensive care measures.

The ultrafiltration rate UFR of a dialyzer increases in proportion to the prevailing transmembrane pressure TMP, where transmembrane pressure is the pressure difference between the average pressure on the blood end and the average pressure on the dialysate end. The ultrafiltration coefficient indicates the amount of fluid removal (ultrafiltration amount) that can be achieved per hour and per mm Hg transmembrane pressure (dimension: mL/h•mm Hg). The ultrafiltration coefficient UFK and the desired fluid removal thus yield the transmembrane pressure TMP to be established.

To increase the patient's safety, existing blood treatment machines typically have a safety device which monitors the transmembrane pressure during the blood treatment to determine whether it exceeds an upper limit or drops below a lower limit, said limits defining a window of safety. An alarm is triggered on leaving this window. Reaching the upper limit may indicate blockage of the dialyzer, and reaching the lower limit may indicate a leak in the fluid system. In a blood treatment with a constant ultrafiltration rate UFR, the window of safety is set manually before starting the blood treatment on the basis of measured transmembrane pressure values. However, if the ultrafiltration rate changes during the blood treatment, the window must be readjusted. Known blood treatment machines allow for a stepwise ultrafiltration profile to be selected so that the window may be automatically readjusted on the basis of new measured values. However, centering the window after a sudden change in ultrafiltration rate generally takes more than one minute with such known devices.

If the ultrafiltration rate is to be regulated continuously, the window must be readjusted constantly. However, if centering the window takes more than one minute, the protective function may be eliminated entirely or at least in part.

German Patent Application No. 34 16 057 A1 describes a hemodialysis machine having a program-controlled device for producing a variable composition of the dialysis fluid. A check is performed during the treatment to determine whether the conductivity of the dialysis fluid is within a predefined window. The conductivity monitoring window is shifted with a change in the composition of the dialysis fluid thereby necessitating readjustment.

German Patent No. 42 39 937 C2 discloses a monitoring a device for hemodialysis equipment intended to prevent ultrafiltration rates that would be harmful to a patient. The disclosed device monitors transmembrane pressure to determine the existence of an undesirable ultrafiltration rate. However, the disclosed device is not suited to reliably monitor transmembrane pressure when the ultrafiltration rate is not constant.

SUMMARY OF THE INVENTION

The present invention is designed to overcome the deficiencies of the prior art discussed above. It is an object of the present invention to create a safety device for an extracorporeal blood treatment machine that is adapted to allow transmembrane pressure to be accurately monitored even with a variable ultrafiltration rate.

It is a further object of the invention is to provide a method of increasing the safety of an extracorporeal blood treatment machine.

In accordance with the illustrative embodiments, demonstrating features and advantages of the present invention, there is provided a safety device for an extracorporeal blood treatment machine of the type that includes an exchange unit divided into first and second chambers by a semipermiable membrane and an ultrafiltration device adapted to remove ultrafiltrate from the exchange unit at varying ultrafiltration rates. The safety device includes a measuring device for measuring transmembrane pressure TMP of the exchange unit, an establishing device for establishing an upper limit $L_1$ and a lower limit $L_2$ for a transmembrane pressure TMP, and a comparing device for comparing a measured transmembrane pressure TMP with the at least one of the upper limit $L_1$ and lower limit $L_2$. The establishing device includes a computer unit for calculating a transmembrane pressure at a preset ultrafiltration rate and for calculating the upper and lower limit $L_1$ and $L_2$ transmembrane pressures on the basis of the calculated transmembrane pressure. The comparing device is in electrical communication with the measuring device. The present invention also relates to a method of increasing the safety of an extracorporeal blood treatment machine.

Other objects, features and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawing a form which is presently preferred; it being understood that the invention is not intended to be limited to the precise arrangements and instrumentalities shown.

FIG. 1 is a schematic diagram of a hemodialysis machine that includes the safety device of the present invention.

DETAILED DESCRIPTION OF THE PREFERRED EMBODIMENT

The present invention relates to a safety device for an extracorporeal blood treatment machine preferably used in hemodialysis, hemofiltration or hemodiafiltration of a patient. The safety of a patient is increased by establishing an upper limit and/or a lower limit for the transmembrane pressure independently of the measured transmembrane pressure. The upper and/or lower limit is determined on the basis of the calculated transmembrane pressure. Thus, the limits can be reset without any time lag after a change in ultrafiltration rate. There is no risk of the protective function being partially or entirely disabled because of a time lag.

It is advantageous if both an upper limit and a lower limit are established for the transmembrane pressure. The upper and lower limits define a window that is readjusted as a function of the ultrafiltration rate during the treatment. In principle, it is also possible to set only an upper limit or a lower limit.

The transmembrane pressure TMP established at a preselected ultrafiltration rate UFR can be determined from the quotient of the ultrafiltration rate UFR and the ultrafiltration coefficient UFK. The ultrafiltration coefficient UFK is advantageously calculated by dividing the ultrafiltration rate UFR established at a certain time by the transmembrane pressure TMP measured at that time. The measurement of the transmembrane pressure at a certain ultrafiltration rate UFR is preferably performed before or at the start of the blood treatment. In principle, however, it is also possible for this calculation to be based on the ultrafiltration coefficient UFK given by the manufacturer of the exchange unit.

The limit values which define the window can be calculated from the sum or the difference in the calculated transmembrane pressure and a percentage amount (coefficient) of the transmembrane pressure. For example, the actual transmembrane pressure should not be more than 10% above or below the calculated transmembrane pressure. During the treatment, the window is shifted toward larger or smaller values as a function of the ultrafiltration rate without changing the width of the window.

In the preferred embodiment, an alarm is triggered if the transmembrane pressure exceeds the upper limit or drops below the lower limit. It is contemplated that additional measures can be utilized to prevent any risk to the patient.

The safety device for an extracorporeal blood treatment machine includes a device for setting the upper and/or lower limits for the transmembrane pressure TMP and a device for comparing the measured transmembrane pressure with the upper and/or lower limits. The device for setting the upper and/or lower limit for the transmembrane pressure has a calculating unit which calculates the transmembrane pressure established at the given ultrafiltration rate and determines the upper and/or lower limit on the basis of the calculated transmembrane pressure. This calculation can be performed with a microprocessor which is typically present in known extracorporeal blood treatment machines.

Referring now to the drawing in detail wherein like reference numerals have been used throughout the various figures to designate like elements, there is shown in FIG. 1 a schematic diagram of the essential components of a hemodialysis machine combined with the safety device 28 of the present invention.

The safety device 28 can be part of the hemodialysis machine or it may be a separate unit which is connected to an existing hemofiltration device.

The hemodialysis machine preferably includes a dialyzer 1, which is divided by a semipermeable membrane 2 into a blood chamber 3 and a dialysis fluid chamber 4. Blood chamber 3 is connected to an extracorporeal blood circuit 5. Dialysis fluid chamber 4 is connected to a dialysis fluid circuit 6. A blood supply line 7 leads from the patient to the inlet of blood chamber 3 of dialyzer 1, and a blood outlet line 8 leads from the outlet of the blood chamber back to the patient. A blood pump 9 is connected to the blood supply line.

A dialysis fluid supply line 11 leads from a dialysis fluid source 10 to the inlet of the first balancing chamber 12 of a balancing unit 13 and from the outlet of the first balancing chamber 12 to the inlet of the dialysis fluid chamber 4 of dialyzer 1. A dialysis fluid outlet line 15 leads from the outlet of dialysis fluid chamber 4 to the second balancing chamber 16 of balancing unit 13, and from the outlet of that chamber to a drain 17. Upstream from balancing unit 13, a dialysis fluid pump 14 is connected to dialysis fluid outlet line 15.

Upstream from second balancing chamber 16 of balancing unit 13, an ultrafiltration line 18 branches off from dialysis fluid outlet line 15 and leads to an ultrafiltrate container 19. An ultrafiltrate pump 20 is connected to the ultrafiltration line 18 to remove the ultrafiltrate.

As long as ultrafiltrate pump 20 is not running, the balancing unit 13 prevents a net exchange of fluid between blood circuit 5 and dialysis fluid circuit 6. No ultrafiltration takes place under these circumstances. Ultrafiltration does not begin until the ultrafiltrate pump is activated. When activated, the ultrafiltrate pump withdraws fluid from dialysis fluid chamber 4 of dialyzer 1 in a controlled manner. The ultrafiltration rate UFR depends on the delivery rate of ultrafiltrate pump 20 which is connected by a control line 21 to a control device 22. The control device 22 changes the ultrafiltration rate UFR as a function of the blood volume of the patient, for example. The components belonging to the ultrafiltration device are labeled with reference number 23.

The safety device 28 preferably includes a measuring device 24 for measuring the transmembrane pressure TMP, a device 25 for setting an upper and lower limit for the transmembrane pressure TMP, a device 26 for comparing the measured transmembrane pressure TMP to the upper and lower limits and an alarm device 27.

The measuring device 24 is connected by a first data line 29 to a pressure meter 30 for measuring the pressure $P_{Di}$ at the inlet of the dialysis fluid chamber 4 and by data line 31 to a pressure meter 32 for measuring the pressure $P_{Do}$ at the outlet of the dialysis fluid chamber 4 of the dialyzer. The measuring device 24 is connected by a data line 33 to a pressure meter 34 for measuring the pressure $P_{Bi}$ at the inlet of blood chamber 3 of the dialyzer and is connected by a data line 35 to a pressure meter 36 for measuring the pressure $P_{Bo}$ at the outlet of blood chamber 3 of the dialyzer 1. The measuring device calculates the transmembrane pressure during the blood treatment from the measured pressure values at the inlet and outlet of dialyzer 1 on the blood end and on the dialysate end as follows:

$$TMP = \frac{P_{Bi} + P_{Bo}}{2} - \frac{P_{Di} + P_{Do}}{2} \tag{1}$$

The transmembrane pressure TMP can also be calculated as follows:

$$TMP = P_{Bo} - P_{Do} + \text{offset}(Q_B, Q_D) \tag{2}$$

According to equation (2), the transmembrane pressure TMP can be calculated from the pressure $P_{Bo}$, $P_{Do}$ at the outlet of blood chamber 3 and dialysis fluid chamber 4 of dialyzer 1 and from the blood flow $Q_B$ and dialysis fluid flow $Q_D$. The offset function depends only on these flows and takes into account the pressure drops along the dialyzer chambers. The measuring device 24 is connected to a comparator (comparing device) 26 by a data line 37. Comparator 26 compares the measured transmembrane pressure value during the blood treatment with the upper and lower limits that define a window. When the transmembrane pressure exceeds the upper limit or drops below the lower limit, the comparator 26 generates an alarm signal which is received by an alarm device 27 over a data line 38. The alarm device delivers an acoustic and/or visual alarm so that the necessary measures can be taken for establishing a status that is tolerable for the patient.

The upper and lower limits for the transmembrane pressure TMP are established as a function of the ultrafiltration rate during treatment with device 25. When the ultrafiltration rate UFR changes, the window is readjusted. Over data line 39, device 25 receives the ultrafiltration rate UFR preset by the control device 21. Device 25 has a computer unit (microprocessor) 25a incorporated therewith. The computer unit 25a is adapted to calculate the upper and lower limits for the transmembrane pressure TMP. Calculation of the limits is described in detail below.

At the start of the treatment, the ultrafiltration coefficient UFK is calculated in the computer unit 25a from a transmembrane pressure $TMP_{mi}$ measured with measuring device 24 and the ultrafiltration rate UFR preset by control device 21 as follows:

$$UFK = \frac{UFR}{TMP_{mi}} \quad (3)$$

During the treatment, the computer unit 25a calculates the transmembrane pressure $TMP_c$ to be expected at the ultrafiltration rate UFR preset by control device 22 on the basis of the previously calculated ultrafiltration coefficient UFK and the ultrafiltration rate UFR as follows:

$$TMP_c = \frac{UFR}{UFK} \quad (4)$$

The actual transmembrane pressure may only be above or below the transmembrane pressure calculated in accordance with (4) by a certain percentage. The computer unit 25a calculates the upper and lower limits $L_1$ and $L_2$ from the calculated transmembrane pressure $TMP_c$ and a first and second coefficients $K_1$, $K_2$ as follows:

$$L_1 = TMP_c + K_1 \cdot TMP_c \quad (5)$$

$$L_2 = TMP_c - K_2 \cdot TMP_c \quad (6)$$

First and second coefficient $K_1$ and $K_2$ are established in accordance with a predetermined percentage(s) to allow values for the upper and lower limits $L_1$ and $L_2$ to be obtained that will not harm a patient undergoing treatment.

The comparator 26 receives the upper and lower limit transmembrane pressures $L_1$, $L_2$ over data line 38 and compares a transmembrane pressure value $TMP_m$ measured with measuring device 24 with these upper and lower limits. The window limits are preferably calculated at the shortest possible intervals during the treatment. Several calculated values may be used to determine the expected transmembrane pressure, and a statistical analysis is performed on these values by known methods.

Calculation of the transmembrane pressure $TMP_c$ according to equation (4) presupposes that after a change in ultrafiltration rate UFR, the transmembrane pressure is established at the new value without any time lag. In practice, however, the new transmembrane pressure TMP is established with a time constant which depends on the ultrafiltration coefficient UFK and the compliance of the closed fluid system (enclosed gas spaces, elastic tubing). The readjustment function of the transmembrane pressure is an exponential function of the solution to a differential equation and depends on the ultrafiltration rate UFR and ultrafiltration coefficient UFK. Taking into account the relaxation over time due to the compliance, the readjustment function of the transmembrane pressure $\Delta TMP_i$ is determined by an exponential function and iteratively as follows:

$$\Delta TMP_i = (1 - e^{-T/r})(UFR_{i-1} - UFR_0)/UFK + e^{-T/r}\Delta TMP_{i-1} \quad (7)$$

The change in TMP is integrated over discrete time increments T of about 5 sec, for example. The relaxation constant r is calculated on the basis of the ultrafiltration coefficient UFK and the known (because it is measured in advance) compliance of the system (information which is stored in the instrument for various treatment modes). $\Delta TMP_{i-1}$ is the readjustment function of the transmembrane pressure at the previous time increment. $UFR_{i-1}$ is the ultrafiltration rate at the previous time increment and $UFR_0$ is the ultrafiltration rate at the start of the treatment.

The first term in equation (7) provides a constant contribution to the change in the ultrafiltration rate UFR and the second term provides the actual exponential time expansion. The second term converges toward a fixed value (over time). The static transmembrane pressure is obtained in this convergence. $\Delta TMP_i$ is added to the calculated transmembrane pressure $TMP_c$ to adjust for any time lag attributed to the change in the ultrafiltration rate.

The present invention may be embodied in other forms without departing from the spirit or essential attributes thereof and accordingly reference should be made to the claims rather than to the foregoing specification as indicating the scope thereof.

What is claimed is:

1. A method of increasing the safety of an extracorporeal blood treatment machine of the type that includes an exchange unit divided into first and second chambers by a semipermeable membrane, and an ultrafiltration device adapted to remove ultrafiltrate from the exchange unit at an ultrafiltration rate, wherein the ultrafiltration device includes a means for adjusting the ultrafiltration rate which can be varied during a blood treatment, the method comprising the steps of:

varying the ultrafiltration rate during the blood treatment;

continuously calculating a transmembrane pressure $TMP_c$ at a preset ultrafiltration rate UFR from the quotient of the preset ultrafiltration rate UFR and an ultrafiltration coefficient UFK;

continuously calculating at least one of an upper limit transmembrane pressure $L_1$ and a lower limit transmembrane pressure $L_2$ on the basis of the calculated transmembrane pressure $TMP_c$, wherein the upper limit transmembrane pressure $L_1$ and the lower limit transmembrane pressure $L_2$ are calculated as a function of the ultrafiltration rate;

measuring a transmembrane pressure $TMP_m$ of the exchange unit, and comparing the measured transmembrane pressure $TMP_m$ with the at least one of the upper limit transmembrane pressure $L_1$ and the lower limit transmembrane pressure $L_2$.

2. The method of claim 1 wherein the ultrafiltration coefficient UFK is calculated from the quotient of the preset ultrafiltration rate UFR and a transmembrane pressure $TMP_{mi}$ at a predetermined time.

3. The method of claim 1 further comprising the step of:

continuously calculating an upper limit transmembrane pressure $L_1$ in accordance with the following equation:

$$L_1 = TMP_c + K_1 \cdot TMP_c$$

wherein $TMP_c$=the calculated transmembrane pressure;

$K_1$=a coefficient.

4. The method of claim 1 further comprising the step of:

continuously calculating a lower limit transmembrane pressure $L_2$ in accordance with the following equation:

$$L_2 = TMP_c - K_2 \cdot TMP_c$$

wherein $TMP_c$=the calculated transmembrane pressure;

$K_2$=a coefficient.

5. The method of claim 1 further including the step of triggering an alarm if the measured transmembrane pressure $TMP_m$ exceeds the upper limit transmembrane pressure $L_1$ or falls below the lower limit transmembrane pressure $L_2$.

* * * * *